United States Patent [19]

Hagedorn et al.

[11] Patent Number: 5,756,809
[45] Date of Patent: May 26, 1998

[54] PROCESS FOR THE PREPARATION OF (2RS,3RS)-3-(2'-AMINOPHENYLTHIO)-2-HYDROXY-3-(4"-METHOXYPHENYL)-PROPIONIC ACID METHYL ESTER

[75] Inventors: Ferdinand Hagedorn; Helmut Fiege, both of Leverkusen, Germany

[73] Assignee: Bayer Aktiengesellschaft, Leverkusen, Germany

[21] Appl. No.: 742,074

[22] Filed: Nov. 1, 1996

[30] Foreign Application Priority Data

Nov. 9, 1995 [DE] Germany .................. 195 41 717.8

[51] Int. Cl.$^6$ ............................................. C07C 149/40
[52] U.S. Cl. ............................................. 560/17
[58] Field of Search ................................. 560/17

[56] References Cited

U.S. PATENT DOCUMENTS 4,908,469  3/1990  Martin ........................ 560/17

FOREIGN PATENT DOCUMENTS 0609031  8/1994  European Pat. Off. .

OTHER PUBLICATIONS

Journal of the Chemical Society, Perkin Transactions 1, Nr. 3, Mar. 1985, Letchworth, GB, Seiten 421–427, XP002033505, T. Hashiyama, et al.: "Reaction of 3-phenylglycidic esters. Part 2. Stereo–and regioselectivity in the oxirane ring opening of methyl trans-3-(4-methoxyphenyl)glycidate with various thiophenols and the effects of solvent and temperature" * Seite 426, linke Spalte *.

T. Hashiyama, et al., Reaction of 3-Phenylglycidic Esters. Part 1.+ Stereoselective Opening of the Oxirane Ring of trans-3-Phenylglycidic Esters with 2-Nitrothiophenols and the Effect of Various Catalysts Thereon, J. Chem. Soc. Perkin Trans. I, pp. 1725–1732,(1984).

H. Kugita, et al., Synthesis of 1,5-Benzothiazepine Derivatives. I, Chem. Pharm. Bull., vol. 18, pp. 2028–2037,(1970).

Primary Examiner—Samuel Barts
Attorney, Agent, or Firm—Sprung Kramer Schaefer & Briscoe

[57] ABSTRACT

(2RS,3RS)-3-(2'-aminophenylthio)-2-hydroxy-3-(4"-methoxyphenyl)-propionic acid methyl ester, an important precursor for the preparation of the pharmaceutical active substance diltiazem, is obtained in a particularly high stereoselectivity and yield by addition of o-aminothiophenol onto 3-(4'-methoxyphenyl)-glycidic acid methyl ester if the reaction is carried out in the presence of alkali metal salts of weak acids in the presence of catalytic amounts of iron compounds.

8 Claims, No Drawings

PROCESS FOR THE PREPARATION OF (2RS,3RS)-3-(2'-AMINOPHENYLTHIO)-2-HYDROXY-3-(4"-METHOXYPHENYL)-PROPIONIC ACID METHYL ESTER

The present invention relates to an improved process for the preparation of (2RS,3RS)-3-(2'-aminophenylthio)-2-hydroxy-3-(4"-methoxyphenyl)-propionic acid methyl ester (also called AHMPE below) by selective addition of o-aminothiophenol onto 3-(4'-methoxyphenyl)-glycidic acid methyl ester (also called MPG ester below).

It is known to prepare AHMPE by addition of unsubstituted o-aminothiophenol onto MPG ester in a non-polar solvent and at elevated temperature. AHMPE is a precursor for the pharmaceutical active compound diltiazem (cf. Chem. Pharm. Bull. 18, 2028 (1970)).

The preparation of AHMPE from MPG ester and o-aminothiophenol proceeds in accordance with the following equation:

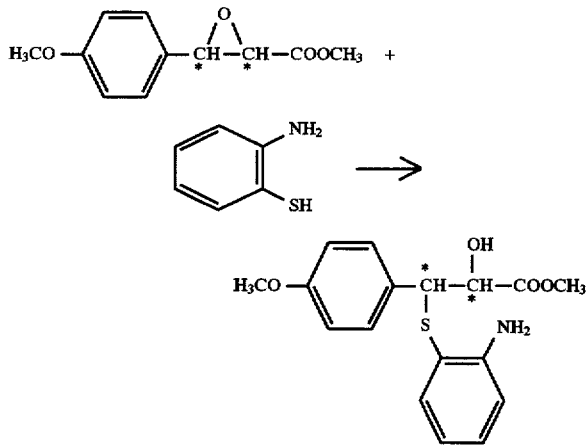

European Laid-Open Specification 609 031 describes a process in which the addition of o-aminoalkylaminothiophenol onto MPG ester to give the threo form of the ester adduct is carried out in the presence of di- or trivalent iron ions.

However, previous studies have shown that iron(II) chloride and iron(III) chloride do not have a catalytic action in the addition of o-nitrothiophenol onto phenylglycidyl esters to give the threo form of the ester adduct. Rather, tin compounds have been found to be active catalysts for this reaction (cf J. Chem. Soc. Perkin Trans, I, 1984, 1725, in particular Table 4 page 1728).

Our own experiments have shown (cf. comparison example 2) that if highly purified MPG ester is employed in the addition of o-aminothiophenol in the absence of iron salts, a high stereoselectivity of the reaction is achieved. However, the provision of highly purified MPG ester requires considerable effort, because, for example, several reprecipitations and/or recrystallizations have to be carried out.

In the customary preparation of MPG ester from anisaldehyde and methylchloroacetate in the presence of sodium methylate with the crude MPG. ester subsequently being taken up from the reaction mixture with a non-polar solvent, for example toluene or xylene, traces of alkali metal salts of weak acids remain in the organic phase even with intense extraction of the solution of the crude MPG ester with water (cf comparison example 1). The MPG ester, which is accessible for this purification without particular effort, comprises traces of, for example, sodium acetate and/or sodium 3-(4'-methylphenyl)-glycidate.

It has now been found that even a few ppm of alkali metal salts of weak acids during the addition of o-aminothiophenol onto MPG ester guide the reaction towards the undesirable stereoisomeric AHMPE of the erythro form. This melts at a significantly lower temperature than the desired threo-AHMPE and has a high dissolving power for the threo product. If MPG ester comprising a few ppm of alkali metal salts of a weak acid is employed, losses in yield of the threo-AHMPE at a scarcely suspected level occur in this manner (cf. Examples 2 to 7).

A process has now been found for the preparation of (2RS, 3RS)-3-(2'-aminophenylthio)-2-hydroxy-3-(4"-methoxyphenyl)-propionic acid methyl ester by addition of o-aminothiophenol onto 3-(4'-methoxyphenyl)-glycidyl methyl ester, which comprises carrying out the reaction in the presence of alkali metal salts of weak acids in the presence of catalytic amounts of iron compounds.

1 to 200 ppm of iron compounds, calculated as iron and based on the o-aminothiophenol, can be employed, for example, in the process according to the invention.

This amount is preferably in the range of 1 to 100 ppm, and is in particular 1 to 20 ppm. The optimum amount of iron compounds depends on the content of alkali metal salts of weak acids in the MPG ester employed, and if appropriate can be determined by simple routine experiments.

All compounds which are soluble in the reaction mixture in the required concentration are suitable in principle for the process according to the invention. Salts containing di-and trivalent iron, for example iron(III) sulfate pentahydrate, iron(II) sulfate, iron(III) chloride, iron(II) chloride and iron salts of organic acids, are preferred. Complex iron compounds, for example iron phthalocyanine and iron acetoacetonate, are also suitable for this purpose. Individual iron compounds or mixtures of several iron compounds can be employed.

The iron compounds can be added to the reaction mixture in solid form, in suspension or in solution. They can also be added to the reaction mixture as a solution in the o-aminothiophenol to be reacted or in solution in the MPG ester to be reacted or as a solution in both. Non-polar solvents, for example, are suitable as the reaction medium for carrying out the process of the present invention. Toluene and xylene are preferred.

When carrying out the addition reaction it is possible to proceed, for example, by dissolving o-aminothiophenol and MPG ester, together with the catalytic amount of iron compounds, in toluene or xylene, heating the solution to the reaction temperature and reacting it at this temperature while stirring.

Another method for carrying out the reaction comprises heating a solution of the MPG ester in a non-polar solvent to the reaction temperature and introducing o-aminothiophenol containing iron compounds into the reaction mixture at this temperature. If only iron-free o-aminothiophenol is available, the small amount of iron compounds can already be admixed to the solution of the MPG ester before heating.

A process variant in which an o-aminothiophenol containing iron compounds, if appropriate dissolved in a non-polar solvent, is heated and the solution of the MPG ester is added at the reaction temperature is also suitable.

Since the addition reaction proceeds exothermically, it is advantageous to control the temperature of the reaction mixture by metering in one of the reaction partners in each case.

The reaction can be carried out, for example at 80° to 150° C., preferably at 90° to 120° C. If the temperatures are too low, the reaction proceeds very slowly and not very selectively.

The reaction time can be, for example, 1 to 12 hours, preferably 2 to 8 hours, particularly preferably 3 to 5 hours. Longer reaction times are in general not critical, because the composition of the reaction mixture scarcely changes further when the reaction has been carried out.

If appropriate, o-aminothiophenol or MPG ester can be employed in excess, for example in an amount of up to 2 mol per mol of the other reaction partner. A molar ratio of o-aminothiophenol to MPG ester of 0.9:1 to 1.1:1, in particular a stoichiometric ratio of amounts, is preferably used.

The reaction mixture can comprise, for example, 5 to 2000 ppm of alkali metal salts of weak acids, which in general are entrained by MPG esters which have not been purified in a particular manner.

As already stated, from very pure MPG ester which has been freed from traces of basic impurities and pure o-aminothiophenol, it is possible to prepare the desired threo-AHMPE with a high yield and high selectivity in a non-polar solvent without addition of iron compounds. However, expensive purification steps, for example several recrystallizations or reprecipitations of the MPG ester, for example from aqueous isopropanol (cf. comparison example 2), or very intensive extraction of the solution of the MPG ester with water and subsequent drying of the solution, are a prerequisite of this. In spite of such measures, traces of alkali metal salts of weak acids remaining in the MPG ester or solution thereof cannot be avoided in all cases. The preparation process for threo-AHMPE can be simplified considerably by the presence, according to the invention, of iron compounds during the reaction, which leads to savings in costs and a reduction in environment-polluting quantities of waste water.

Another improvement to the prior art is achieved if the aqueous solution of an alkali metal salt of o-aminothiophenol obtained by alkaline cleavage of benzothiazole is first acidified to a pH of 4 to 6 in the presence of a small amount of a non-polar solvent, and the organic phase, which separates very readily from the aqueous solution, is separated off and, after extraction with water to remove residual salt after incipient distillation under a weak vacuum to remove adhering water and low-boiling impurities, is then reacted at elevated temperature with a solution of the MPG ester in the same organic polar solvent in the presence of iron. The amount of solvent required for this combination of measures is not more than 12% of the volume of the crude o-aminothiophenol. The acidification can be carried out, for example, to a pH of 4.5 to 5.5 with sulfuric acid and in the presence of toluene or xylene. The incipient distillation can be carried out, for example, at temperatures of up to 50° C.

Such combinations of measures lead to an improved phase separation during the preparation of o-aminothiophenol and save a time-consuming yield-diminishing distillation of the entire amount of o-aminothiophenol to be employed in the reaction with MPG ester.

The following examples illustrate the present invention.

EXAMPLES

Percentage data are percentages by weight, unless stated otherwise.

Comparison Example 1

(Use of MPG ester containing alkali metal salts of weak acids, no addition of iron compounds)

20.9 g of 3-(4'-methoxyphenyl)-glycidic acid methyl ester which had a sodium content of 440 ppm (only 90 ppm of which are present as sodium chloride) were dissolved in 100 ml of xylene. The solution was extracted twice with 50 ml of water each time and residual water was removed by heating to a bottom temperature of not more than 145° C. 14.4 g of iron-free o-aminothiophenol were introduced, while stirring, into the solution, which had been cooled to 115° C., and the mixture was heated at 115° C. for 4 hours, while stirring further. After cooling to 790° C., HPLC analysis of the clear solution showed a content of 86.4% of the desired threo addition compound.

Example 1

220.9 g of 3-(4'-methoxyphenyl)-glycidic acid methyl ester having a content of sodium of 440 ppm, only 90 ppm of which was sodium chloride, were dissolved in 100 ml of xylene. The solution was extracted twice by stirring with in each case 50 ml of water. After separation of the phases, the solution was heated to 145° C. under nitrogen, while removing residual water from the circulation. The resulting clear solution was cooled to 115° C., 2.0 mg of iron(III) chloride and 14.4 g of o-aminothiophenol were added and the mixture was kept at 115° C. for a further 4 hours, while stirring. After cooling to 70° C., 186.0 g of a solution having a content, determined by HPLC, of 16.6% of the desired threo-AHMPE, corresponding to 92.8% of theory, and 1.04% of erythro-AHMPE, corresponding to 5.8% of theory, were obtained. After the solvent had been removed, the residue had been taken up in toluene and the product had been crystallized, filtered off with suction and dried, the yield was 29.2 g of a 96.7% pure threo-AHMPE, corresponding to 95% of theory. A 99.4% pure threo-AHMPE was obtained by reprecipitating in toluene.

Comparison example 2

(Use of highly pure MPG ester, no addition of iron compounds)

69.6 g of o-aminothiophenol (98.9% pure) and 105.2 g of 3-(4'-methoxyphenyl)-glycidic acid methyl ester (100% pure, obtained by several recrystallizations from isopropanol/water) in 500 ml of toluene were initially introduced into a 1l stirred flask and heated to 115° C. under nitrogen. The clear solution was stirred at this temperature for 4 hours and then cooled. The yield of crude solution was 574.7 g, with a content, determined by HPLC, of 26.7% of threo-AHMPE, corresponding to 91.8% of theory, and a 1.7% of erythro-AHMPE, corresponding to 5.8% of theory.

Examples 2 to 7

Examples 2 to 7 in each case comprise two experiments, the addition of iron-free o-aminothiophenol onto highly purified MPG ester in xylene with the addition of small amounts of sodium acetate or sodium 3-(4'-methoxyphenyl)-glycidate being carried out in the first (a) experiment, not according to the invention). In the second experiment comparable to this in each case (b) experiment, according to the invention), as well as the addition of sodium acetate or sodium 3-(4'-methoxyphenyl)-glycidate, o-aminothiophenol with a content of 5 ppm of iron in the form of iron(III) chloride was used.

Procedure for the experiments:

In each case 14.4 g of o-aminothiophenol (96% pure), 20.9 g of 3-(4'-methoxyphenyl)- glycidic acid methyl ester (recrystallized, 100% pure) and the particular addition of sodium salt stated were heated to 115° C. in 100 ml of xylene under nitrogen and the mixture was stirred at this temperature for 4 hours. After the solution had been cooled, the result was determined by an HPLC analysis.

Sodium acetate was added in Examples 2 to 5 and sodium 3-(4'-methoxyphenyl)-glycidate was added in Examples 6 and 7.

The details and results can be seen from Table 1.

It can be seen from Table 1 that the yields of threo+erythro-AHMPE and the contents of the desired threo-AHMPE in the total addition product are always significantly higher if iron salts are added than in the absence of iron salts.

|  |  | Yield in the crude solution (%) | | | | Sum of | | | |
|---|---|---|---|---|---|---|---|---|---|
|  |  | threo | | erythro | | threo + erythro (%) | | Threo:erythro ratio | |
| Example No. | Na Salt (ppm) | a) without Fe | b) with Fe | a) without Fe | b) with Fe | a) without Fe | b) with Fe | a) without Fe | b) with Fe |
| 2 | 32.7 | 83.6 | 93.3 | 8.6 | 5.6 | 92.2 | 99.9 | 9.7 | 14.1 |
| 3 | 130.7 | 79.5 | 90.2 | 19.3 | 6.8 | 92.8 | 97.0 | 3.8 | 13.3 |
| 4 | 261.5 | 71.9 | 89.0 | 18.6 | 7.4 | 90.5 | 96.4 | 3.9 | 12.0 |
| 5 | 614.5 | 32.9 | 77.0 | 35.4 | 9.9 | 68.3 | 86.9 | 0.9 | 7.8 |
| 6 | 201.0 | 77.2 | 88.5 | 12.4 | 7.2 | 89.6 | 95.7 | 6.2 | 12.3 |
| 7 | 808.6 | 76.4 | 83.6 | 15.4 | 12.3 | 91.8 | 95.9 | 5.0 | 6.8 |

Example 8

270.1 g of a 30% strength sodium methylate solution in methanol and additionally 50 ml of methanol were initially introduced into a stirred flask and cooled to 0° C., while stirring. 137.5 g of anisaldehyde (99% pure) and 115.1 g of methylchloroacetate (99% pure) were added dropwise from two dropping funnels, separately from one another but simultaneously, in the course of 2 hours at a constant 0° C., while stirring. The reaction mixture was then subsequently stirred at 0° C. for 4 hours. Thereafter, 35 ml of glacial acetic acid were added dropwise, with further cooling, during which the temperature of the mixture did not exceed +5° C. Thereafter, 800 ml of toluene were added, the mixture was thoroughly stirred vigorously, and 500 ml of water was then added. The mixture was thoroughly stirred vigorously, the phases were separated, the toluene phase was washed free from chloride three times with 100 ml of water each time and a vacuum distillation was carried out without delay at 45° C. under 95 mbar for azeotropic dehydration of the solution. 751.3 g of solution having a content of 23.9% of the desired 3-(4'-methoxyphenyl)-glycidic acid methyl ester, corresponding to 86.2% of theory, were obtained.

435.9 g of the resulting toluene solution of the glycidyl ester were heated to 115° C., while gassing with nitrogen. 73.2 g of o-aminothiophenol (obtained as described in Example 9, but without removal of the solvent, and with brief incipient distillation to remove water) which comprises 5 ppm of iron in the form of iron(III) chloride were added dropwise at this temperature in the course of 10 minutes. The mixture was then heated under reflux for 4 hours and at the same time water was removed from the circulation. 60 ml of a toluene solution having a content of 26.2% of threo-AHMPE, corresponding to 90.6% of theory, were obtained. The solution furthermore comprised 1.8% of eythro-AHMPE, corresponding to 6.4% of theory. The toluene solution was cooled to 50° C., seed crystals of threo-AHMPE were added and the mixture was cooled to 5° C. After complete crystallization, the mixture was filtered off with suction at 5° C. and the residue was washed with 75 ml of cooled toluene and then with a solution of 50 ml of methanol and 50 ml of water. After drying, 140.5 g of colorless crystals were obtained, which corresponds to a yield of 84.3% of theory of threo-AHMPE.

Example 9

(Advantageous isolation of o-aminothiophenol from a reaction mixture)

1 kg of o-aminothiophenol sodium salt solution (technical grade, about 25% strength), obtained by cleavage of benzothiazole with sodium hydroxide solution at elevated temperature, was initially introduced into a stirred flask with a bottom valve, under nitrogen. 310 g of 48% strength aqueous sulfuric acid were added dropwise, from a dropping funnel, while stirring up to a pH of 4.8, and with control of the temperature, which did not exceed 50° C. 100 ml of toluene were now added, the mixture was thoroughly stirred vigorously and a rapid and good separation between the organic and the aqueous phase was obtained. The lower, aqueous, salt-containing phase was drained off through the bottom valve. After addition of 100 ml of water, the organic phase was thoroughly stirred vigorously and freed from residual dissolved salt in this way. It was then drained off through the bottom valve. 282 g of a pale yellow solution of o-aminothiophenol in toluene were thus obtained. After incipient distillation to remove the solvent under 55 to 58 mbar up to a bottom temperature of 122° C., 198 g of o-aminothiophenol of the following composition (GC) were obtained:

| o-aminothiophenol | 97.3% |
|---|---|
| toluene | 0.8% |
| aniline | 0.2% |
| 2-methylaniline | less than 0.1% |
| isomeric aminothiophenol | 0.1% |
| methylmercaptoaniline | 0.2% |
| 2,2'-diaminodiphenyl disulfide | 0.9% |
| benzothiazole | less than 0.1% |

Such o- aminothiophenol proved to be particularly suitable for the reaction with 3-(4'-methoxyphenyl)-glycidic acid methyl ester in the presence of iron compounds.

We claim:

1. A process for the preparation of (2RS,3RS)-3-(2'-aminophenylthio)-2-hydroxy-3-(4"-methoxyphenyl)-propionic acid methyl ester by addition of o-aminothiophenol onto 3-(4'-methoxyphenyl)-glycidic acid methyl ester, which comprises carrying out the reaction in the presence of an alkali metal salt of a weak acid in the presence of a catalytic amount of an iron compound.

2. The process as claimed in claim 1, wherein iron compounds which contain 2- and/or 3-valent iron are employed.

3. The process as claimed in claim 1, wherein iron(III) sulfate pentahydrate, iron(II) sulfate, iron(III) chloride, iron (II) chloride, iron salts of organic acids and/or complex iron compounds are employed.

4. The process as claimed in claim 1, wherein 1 to 200 ppm of iron compounds, calculated as iron and based on o-aminothiophenol, are employed.

5. The process as claimed in claim 1, wherein the reaction is carried out in a non-polar solvent.

6. The process as claimed in claim 1, wherein the reaction is carried out at 80° to 150° C.

7. The process as claimed in claim 1, wherein the reaction mixture comprises 5 to 2000 ppm of an alkali metal salt of a weak acid.

8. The process as claimed in claim 1, wherein o-aminothiophenol which has been obtained by acidifying the aqueous solution, obtained by alkaline cleavage of benzothiazole, of an alkali metal salt of o-aminothiophenol to a pH of 4 to 6 in the presence of a small amount of a non-polar solvent, separating off the organic phase which separates out and, after extraction with water and incipient distillation under a weak vacuum, freeing it from residual salts, adhering water and low-boiling impurities, is employed.

* * * * *